United States Patent [19]

Miller et al.

[11] Patent Number: 5,028,646
[45] Date of Patent: Jul. 2, 1991

[54] PRESSURE-SENSITIVE ADHESIVE COMPOSITION, TAPE AND DIAPER CLOSURE SYSTEM

[75] Inventors: John A. Miller, St. Paul, Minn.; Egbert A. von Jakusch, Hilden, Fed. Rep. of Germany

[73] Assignee: Minnesota Mining and Manufacturing Company, St. Paul, Minn.

[21] Appl. No.: 437,771

[22] Filed: Nov. 15, 1989

Related U.S. Application Data

[63] Continuation of Ser. No. 227,407, Aug. 4, 1988, abandoned.

[51] Int. Cl.$^5$ ............................................. C08L 93/04
[52] U.S. Cl. ..................................... 524/77; 524/274; 524/311; 524/312; 524/476; 524/482; 524/505; 525/96; 525/98; 428/497; 428/500; 428/516; 428/521; 604/389
[58] Field of Search ............... 524/271, 274, 311, 312, 524/476, 482, 505; 525/96, 98; 428/497, 500, 516, 521; 604/389

[56] References Cited

U.S. PATENT DOCUMENTS

| | | | |
|---|---|---|---|
| 3,239,478 | 3/1966 | Harlan | 428/348 |
| 3,862,068 | 1/1975 | Russell | 524/271 |
| 3,917,607 | 11/1979 | Crosslands et al. | 524/478 |
| 3,932,328 | 1/1976 | Korpman | 524/271 |
| 3,951,149 | 4/1976 | Ness et al. | 128/287 |
| 4,038,346 | 7/1977 | Fenney | 524/505 |
| 4,104,323 | 8/1978 | Hansen | 524/505 |
| 4,136,071 | 1/1979 | Korpman | 524/534 |
| 4,230,842 | 10/1980 | Bullard et al. | 526/185 |
| 4,345,349 | 8/1982 | Flanagan | 412/5 |
| 4,359,551 | 11/1982 | Suda et al. | 524/271 |
| 4,399,249 | 8/1983 | Buildusas | 524/271 |
| 4,418,123 | 11/1983 | Bunnelle et al. | 428/517 |
| 4,556,464 | 12/1985 | St. Clair | 524/274 |
| 4,581,400 | 4/1986 | Kondo | 524/274 |
| 4,655,761 | 4/1987 | Grube et al. | 604/389 |
| 4,683,268 | 7/1987 | Ahner | 525/237 |
| 4,717,749 | 1/1988 | Tang et al. | 524/271 |
| 4,719,261 | 1/1988 | Runnelle et al. | 525/97 |
| 4,732,936 | 3/1988 | Holohan | 525/88 |

FOREIGN PATENT DOCUMENTS

| | | |
|---|---|---|
| 0101961 | 3/1984 | European Pat. Off. |
| 1405786 | 9/1975 | United Kingdom |
| 2114449 | 8/1983 | United Kingdom |
| 2162737 | 2/1986 | United Kingdom |

OTHER PUBLICATIONS

Hercules Product Data Sheet for Piccolastic ® D Resins dated 6-81.
Hercules Product Sheet for Piccotex ® Resins dated 4-82.

Primary Examiner—John Kight, III
Assistant Examiner—Sam A. Acquah
Attorney, Agent, or Firm—Gary L. Griswold; Walter N. Kirn; Carole Truesdale

[57] ABSTRACT

Pressure-sensitive adhesive compositions and an improved refastenable tape closure system comprising a release tape and a fastening tape wherein the fastening tape has a balance of properties such that the tape exhibits a maximum in the peel force between peel rates of 10 cm./minute and 400 cm./minute when peeled from a polyolefin substrate as found in disposable diaper back sheets are disclosed. The adhesive of the fastening tape comprises a specific range of compositions including an elastomeric component based on an A-B-A block copolymer wherein the A blocks are derived from styrene or alphamethylstyrene and the B blocks are derived from isoprene, butadiene, or hydrogenated versions of these or an (AB) block copolymer of the same type of composition in another geometry such as a tapered block copolymer or a radial block copolymer, a solid tackifier resin, a liquid tackifier resin, and an end block reinforcing resin.

7 Claims, 5 Drawing Sheets

PRESSURE-SENSITIVE ADHESIVE COMPOSITION, TAPE AND DIAPER CLOSURE SYSTEM

This is a continuation of application Ser. No. 07/227,407 filed Aug. 4, 1988 now abandoned.

BACKGROUND OF THE INVENTION

The present invention relates to pressure-sensitive adhesive compositions, pressure-sensitive adhesive tapes made therefrom and a refastenable pressure-sensitive adhesive tape closure system for disposable diapers, incontinence garments, and the like.

U.S. Pat. No. 3,951,149 (Ness et al.) discloses a three-tape target closure system for disposable diapers. Such a closure system affords reliable closure and refastenability but also has several disadvantages. These include the higher cost of a three-tape system, greater difficulty in applying three tapes during the manufacture of the diaper, and the potential for misuse on the part of the user.

U.K. Publication GB 2,114,449 (Personal Products) discloses a diaper constructed with a two-tape refastenable closure system. However, the reported peel and quick stick values for this closure system likely make such a closure system unreliable in certain circumstances.

U.K. Publication GB 2,162,737 (Kimberly-Clark) and corresponding U.S. Pat. No. 4,655,761 describe a two-tape refastenable closure system for disposable diapers wherein the fastening tape forms a good bond to the diaper back sheet yet does not tear the film upon subsequent reopening. Further, these references mention the 180 degree peel properties of the fastening tape as being between 400 and 575 grams per inch at a peel rate of 12 inches per minute and between 200 and 400 grams per inch at 400 inches per minute from an embossed, corona treated polyethylene surface as typically used for a disposable diaper cover sheet. The composition of the tape is not specified.

U.S. Pat. No. 4,399,249 (Bildusas) describes a refastenable adhesive composition for polyethylene substrates. The major use for such adhesives is stated to be for resealable food storage bags.

U.S. Pat. No. 3,239,478 (Harlan, Jr.) discloses a type of pressure-sensitive adhesive comprising an A-B-A block copolymer, a solid tackifying resin, and processing oil. However, at high oil contents, adhesives of this type have very poor shear resistance. Further, the formulations described in U.S. Pat. No. 3,239,478 generally do not exhibit a maximum in the peel force for peel rates between 10 and 400 cm/min.

U.S. Pat. No. 3,932,328 (Korpman) describes a three component adhesive system comprising a styrene-isoprene-styrene A-B-A block copolymer, a liquid tackifying resin, and a solid tackifying resin. The solid tackifying resin is of the type prepared from a hydrocarbon stream comprising at least 40% isoprene and/or piperylene, the remainder being other dienes and mono-olefins. As was the case with U.S. Pat. No. 3,239,478, formulations within the specified range generally do not show a maximum in the peel force at a peel rate between 10 and 400 cm/min. However, selected compositions can be found within the formulation range described in U.S. Pat. No. 3,932,328 that do exhibit a maximum in the peel force at a peel rate between 10 and 400 cm/min, but these formulations are found to exhibit poor aging stability. When such formulations are prepared into tape specimens and exposed to a normal atmosphere at 40° C. for one month, a substantial loss in pressure-sensitive tack is observed.

U.S. Pat. No. 4,418,123 (Bunnelle et al.) describes a three-component system consisting essentially of an elastomeric block copolymer, a midblock associating resin, and an end block reinforcing resin. These formulations are at the same time both elastomeric and tacky in nature and are described as self-adhering elastics. Compositions of this nature not only exhibit significantly lower adhesion than the compositions described in the present invention, they also tend to have a higher cost due to the relatively greater amount of the elastomeric component. Further, the preferred range of end block content is higher for the systems described in U.S. Pat. No. 4,418,123 than for the systems of the present invention. That patent also does not teach the use of liquid tackifying resins in conjunction with the other three components nor does it in any way suggest that compositions of the type disclosed would be useful in a refastenable pressure-sensitive tape for diaper closure systems.

U.S. Pat. No. 3,862,068 (Russell) discloses a pressure-sensitive adhesive composition which comprises a resinous rubbery block copolymer of styrene and butadiene or isoprene; a rubber extending petroleum oil; a modified or unmodified rosin, a coumarone-idene resin, a polyterpene resin, a diene-olefin aliphatic hydrocarbon resin, or a polystyrene resin; and a resinous atactic polypropylene.

U.S. Pat. No. 4,038,346 (Feeney) discloses a tackifier composition comprised of both a tackifying resin derived from the polymerization of a mixture of at least one olefin and at least one diolefin as well as an oily polymer distillation cut at a temperature in the range of about 190° C. to about 250° C. of the product of polymerizing a monomer mixture of piperylene and selected monoolefins with the optional addition of dicyclopentadiene and a-methyl styrene. The tackifiers can be used with selected rubbery polymers to achieve adhesive compositions.

U.S. Pat. No. 4,136,071 (Korpman) discloses a pressure-sensitive adhesive which comprises a major proportion of styrene-isoprene-styrene A-B-A block copolymer elastomers and a minor proportion of styrene-isoprene A-B block copolymer elastomers in its elastomeric component and tackifier resins.

U.S. Pat. No. 4,345,349 (Flanagan) discloses hot melt adhesives prepared from 15–30% of an A-B-A block polymer wherein A is a non-elastomeric polymer block derived from the moieties of a monovinyl aromatic hydrocarbon radical and B is an elastomeric polymer block derived from the moieties of a conjugated diene monomer; 5–10% of an ethylene vinyl acetate copolymer containing 17–42% vinyl acetate, wherein the ratio of the block polymer to the ethylene vinyl acetate copolymer is within the range of 1.75:1 to 6:1; 25–40% of at least one resin ester tackifier selected from the group consisting of glycerol and pentaerythritol esters of natural and modified rosins; 25–35% of a was diluent which is solid at room temperature; and 0.5 to 3% of at least one stabilizer.

U.S. Pat. No. 4,359,551 (Suda et al.) discloses a hot-melt pressure-sensitive adhesive composition comprising 100 parts by weight of a block copolymer formed by the graft reaction of at least one block copolymer comprising at least one polybutadiene or polyisoprene block and at least two polystyrene blocks with at least one unsaturated carboxylic acid monomer and/or derivative monomer thereof and 50 to 250 parts by weight of a specific tackifier mixture consisting of a tackifier S comprising at least 50% by weight of a terpene resin having a softening point of 60° C. or more and a tackifier L comprising at least 50% by weight of a terpene resin having a softening point of 30° C. or less and having an S/L mixing weight ratio of 9/1 to 3/7, and optionally 1 to 50 parts by weight of a softening agent.

U.S. Pat. No. 4,556,464 (St. Clair) discloses a cured adhesive composition prepared using a block copolymer containing carbon-carbon double bonds in the endblocks which are crosslinked by crosslinking agent preferentially compatible with the endblock phase of the block copolymer.

U.S. Pat. No. 4,581,400 (Kondo) discloses a rubber composition comprising (a) 100 parts by weight of a rubber selected from the group consisting of natural rubber and synthetic diene rubbers and (b) about 1 to about 30 parts by weight of a rosin derivative comprising a blend of (i) about 15 to 50% by weight of a rosin, (ii) about 10 to about 70% by weight of a polymerized rosin and (iii) not more than about 55% by weight of a rosin pitch, each based on the weight of the rosin derivative.

U.S. Pat. No. 4,717,749 (Tang et al.) discloses pressure-sensitive adhesive compositions comprising (1) a block copolymer of ABA configuration wherein A is a copolymer of alpha-methylstyrene and styrene and the B portion of the polymer is a polydiene; (2) a diblock copolymer of AB type of an amount from 0 to 50 parts per weight per hundred parts of the ABA triblock copolymer; (3) a tackifying resin compatible with block B in the amount of 10 to 200 parts per hundred parts of the block copolymer; (4) a reinforcing resin having a higher softening point than the block A in the ABA polymer in the amount of from about 0 to 100 parts per hundred parts of the ABA block copolymer; and (6) a stabilizer in the amount of 0 to 5 parts per hundred parts by weight of the block ABA block copolymer.

U.S. Pat. No. 4,719,261 (Bunnelle et al.) discloses a hot melt adhesive for elastic banding and a method for utilizing the adhesive. A suitable viscoelastic hot melt pressure-sensitive adhesive is described as typically comprising (1) a rubbery block copolymer which includes a rubbery midblock portion and which is terminated with crystalline vinyl arene blocks, (2) a tackifying resin generally compatible with and generally associated with the midblock portion of the block copolymer, and, optionally, (3) an aromatic, essentially hydrocarbon resin having a glass transition temperature and a softening point above those of the tackifying resin and the endblocks of the block copolymer, which aromatic resin is generally compatible with and generally associated with the aforementioned end blocks.

SUMMARY OF THE INVENTION

The present invention relates to a pressure-sensitive adhesive tape diaper closure system that is particularly advantageous when compared with current closure systems. The system is a two-tape refastenable closure system for disposable diapers and incontinence garments and comprises a release tape and a fastening tape. The fastening tape comprises a backing material such as paper, polyester, polypropylene, and other common pressure-sensitive tape backings. The preferred backing material is polypropylene, especially polypropylene films between 50 microns and 150 microns thick with a fine random embossing pattern on each side. The pressure-sensitive adhesive used on the fastening tape is selected such that the fastening tape exhibits a maximum in the peel force at a peel rate between 10 and 400 cm/min, (log peel rate between about 1.0 and 2.6 cm/min) preferably between 25 and 300 cm/min (log peel rate between about 1.2 and 2.5 cm/min) when peeled from a polyolefin substrate particularly polypropylene and polyethylene films typical of that used for disposable diaper back sheets. Tapes exhibiting such a maximum have been found to be strongly preferred by consumers of disposable diapers. It is theorized that the higher peel forces at low rates discourages the wearer of the garment, typically an infant, from peeling open the closure whereas the decreased peel force at ever increasing peel rates aids the user in removing the closure tape without tearing the diaper back sheet. The back side of the fastening tape is coated with a release coating of a conventional type. In addition, the closure system includes a release tape of conventional design incorporating a film backing coated on one side with a silicone release layer and on the other side with a natural or synthetic rubber-based pressure-sensitive adhesive.

The pressure-sensitive adhesive compositions of the present invention not only exhibit a maximum in the peel force at a peel rate between 10 and 400 cm/min when peeled from a polyolefin substrate such as polypropylene or polyethylene film typical of that used for disposable diaper back sheets, but also show good aging stability when exposed to a normal atmosphere at 40° C. for one month. The formulations which exhibit these properties comprise an A-B-A block copolymer wherein the B blocks are derived from isoprene, butadiene, or hydrogenated versions of these or an (AB) block copolymer of the same type of composition in another geometry such as a tapered block copolymer or a radial block copolymer; a solid tackifier resin; a liquid tackifier resin; and an end block reinforcing resin. The elastomeric component is preferably present in the range from 20% to 50% by weight, more preferably from 25% to 40% by weight. The solid tackifying resin is preferably present in the range from 20% to 60% by weight, more preferably from 25% to 50% by weight. The end block reinforcing resin is preferably present in the range from 2 to 20% by weight, more preferably from 4% to 14% by weight. The liquid tackifying resin is preferably present in the range from 0% to 40% by weight, more preferably from 15% to 30% by weight. The compositions of the invention not only exhibit the maximum in the peel rate vs. peel force curve between 10 and 400 cm/min when peeled from a polyethylene substrate typical of that used for disposable diaper back sheets, but they also show excellent accelerated aging properties, good quick stick, tack, peel, and shear resistance properties. Furthermore, these compositions can be readily processed by either solvent coating processes or conventional hot-melt adhesives coating equipment.

DETAILED DESCRIPTION

Figure 1:
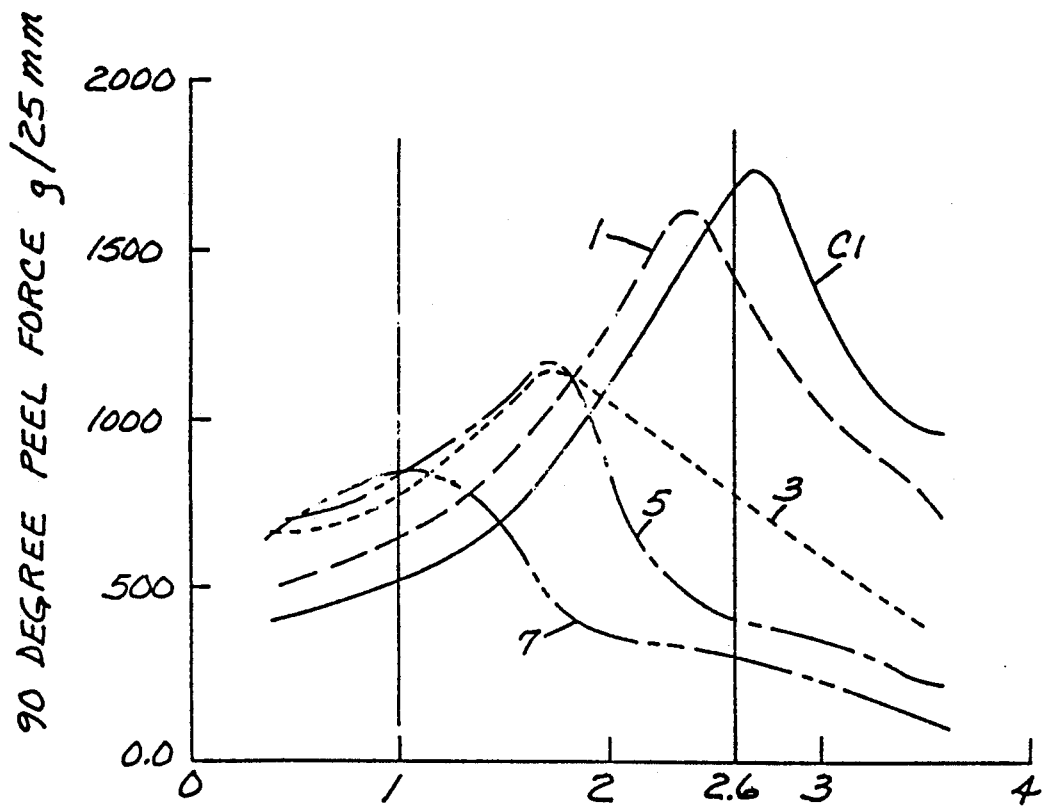
FIG. 1 is a plot of the 90 degree peel force in g/25 cm in relation to the log peel rate in cm/min for the adhesive compositions of Examples 1, 3, 5, and 7 and Comparative Example C1.

The present invention relates to a two-tape diaper closure system comprising a release tape and a fastening tape. The closure system of our invention not only exhibits the maximum in the peel rate vs. peel force curve when the fastening tape is peeled from a polyolefin substrate at between 10 and 400 cm/min (log peel rate between about 1.0 and 2.6 cm/min) as well as excellent accelerated aging properties, but it also exhibits excellent bond security and excellent refastenability. Furthermore, this closure system can be readily applied to disposable diapers by the manufacturer of the diapers. The cost of this closure system is equivalent to conventional two-tape refastenable systems.

The release tape used in the closure system comprises a polypropylene film backing, preferably between 50 and 125 microns thick, with a fine, random matte embossing pattern on one side and a smooth finish on the other side. On the smooth side is coated a release coating, preferably a crosslinked poly(dimethylsiloxane) type. On the matte side of the release tape is coated a pressure-sensitive adhesive that adheres well to nonwoven fabrics typically found as inner liners in disposable diapers such as those formed from fibers of polypropylene, polyethylene, ethylene/vinyl acetate copolymers, and blends of these fibers. Such adhesives are typically blends of natural or synthetic elastomers with one or more tackifying resins and other common pressure-sensitive adhesive additives. The preferred adhesive composition comprises natural rubber between 25% and 50% by weight compounded with a solid polyterpene tackifying resin between 25% and 60% by weight and up to 50% by weight of a liquid hydrocarbon resin. Especially preferred compositions range between 30% and 45% by weight of natural rubber, between 30% and 50% by weight of a polyterpene solid tackifier, and between 15% and 35% by weight of a liquid hydrocarbon resin.

The fastening tape comprises a conventional tape backing such as paper, polyester or polypropylene film backing and a pressure-sensitive adhesive composition of the present invention. The adhesive composition used for the fastening tape comprises an elastomer which is an A-B-A block copolymer wherein the A blocks are derived from styrene or alpha-methylstyrene and the B blocks are derived from isoprene, butadiene, or hydrogenated versions of these or an (AB) block copolymer of the same type of composition in another geometry such as a tapered block copolymer or a radial block copolymer, a solid tackifier resin, a liquid tackifier resin, and an end block reinforcing resin. The elastomeric component is preferably present in the range from 20% to 50% by weight, more preferably from 25% to 40% by weight. The solid tackifying resin is preferably present in the range from 20% to 60% by weight, more preferably from 25% to 50% by weight. The end block reinforcing resin is preferably present in the range from 2 to 20% by weight, more preferably from 4% to 14% by weight. The liquid tackifying resin is preferably present in the range from 10% to 40% by weight, more preferably from 15% to 30% by weight.

The elastomeric component used in the fastening tape for this invention comprises one of a variety of configurations of block copolymers comprising at least two distinct block types. Typical configurations include linear triblock, star, radial, branched, and tapered geometries. The first block is flexible at the service temperature while the second block is usually rigid at the service temperature. The first block comprises polymerized isoprene or butadiene units or hydrogenated versions of these while the second block comprises polymerized styrenic species such as styrene or alphamethylstyrene. The second block is usually present in the range of 8% to 30% by weight of the total block copolymer when the first block is isoprene-based and 20% to 50% by weight when the first block is butadiene-based. The molecular weight of the block copolymer is typically greater than 50,000. Useful block copolymers include an A-B-A linear triblock copolymer of styrene and isoprene ranging from 10% to about 21% styrene such as those commercially available from Shell Chemical Company as KRATON TM 1107 and KRATON TM 1111 or from Nippon-Zeon as QUINTAC TM 3420, 3430, and 3530. Another useful block copolymer is a multiblock copolymer of butadiene and styrene such as those commercially available from Firestone Synthetic Latex and Rubber Company as STERON TM 840A and STERON TM 845A.

The solid tackifying resins suitable for use in this invention belong to several of the commerically important resin classes including rosin esters; hydrogenated rosin esters; polyterpene resins; polymerized hydrocarbon resins based on piperylene, isoprene, and other conjugated dienes containing 4 to 6 carbon atoms as well as hydrogenated versions of these materials; resins from polymerized and hydrogenated C9 hydrocarbon streams; resins from polymerized and hydrogenated dicyclopentadiene species; resins from polymerized and hydrogenated pure monomer species such as styrene, vinyl toluene, alphamethyl styrene; etc. Useful solid tackifying resins include a hydrocarbon resin of polymerized structures derived primarily from a stream of aliphatic petroleum derivatives, both dienes and monoolefins, containing 4 to 6 carbon atoms. Piperylene and isoprene are the most common species. Such resins are commerically available from Exxon Chemical Company as ESCOREZ TM 1310 and from the Goodyear Chemical Company as WINGTACK TM Plus and WINGTACK TM 95. Another useful solid resin comprises predominantly cyclopentadiene species that have been polymerized and hydrogenated. Such solid tackifying resins are available from Exxon Chemical Company as ESCOREZ TM 5380, ESCOREZ TM 5300, and ESCOREZ TM 5320. Another useful solid tackifying resin includes a resin produced from the polymerization and hydrogenation of a pure monomer feedstock comprising styrene, vinyl toluene, and alphamethyl styrene, such as the resins available from Hercules Chemical Company as REGALREZ TM 1094 and REGALREZ TM 1126. Still another solid tackifier resin is a partially hydrogenated rosin ester. Such a resin is available as PERMALYN TM 1105 from Hercules Chemical Company. A tackifying resin for styrene/butadiene block copolymers is a polymerized alpha pinene resin having a softening point of about 100° C. available from Arizona Chemical Company as ZONAREZ TM A-100. A second solid resin for styrene/butadiene block copolymers is a styrenated terpene type resin available from Goodyear Chemical Company as WINGTACK TM 86.

The reinforcing end block resin is an aromatic, essentially hydrocarbon resin which generally has a glass transition temperature higher than the service temperature of the adhesive and often higher than that of the end block of the block copolymer and the solid tackifier resin in the adhesive. Generally, the aromatic resin is compatible with and associated with the vinyl arene end blocks of the block copolymer. It is particularly desirable that the end block resin have a glass transition temperature and a softening point above those of the end block and midblock of the block copolymer. For example, it would ordinarily not be desirable for the softening point of the end block resin to be in the 80°-100° C. range and therefore, end block resins with somewhat higher molecular weights and softening points above 115° C. are typically selected. Typical reinforcing resins suitable for use in the fastening tape for this invention include low molecular weight polymers of styrene and alpha-methylstyrene as well as copolymers of these, coumarone-indenes, polyindenes, and other resins containing mono or polycyclic aromatic groups. Examples of suitable end block resins include KRISTALEX TM 1120 and KRISTALEX TM 5140 available from Hercules Chemical Company, ENDEX TM 155 and ENDEX TM 160, also available from Hercules, and Resin 18-290 available from Amoco Chemical Company. The preferred end block resins for this invention are ENDEX TM 155 and ENDEX TM 160.

The liquid tackifier component suitable for use in the fastening tape for this invention can be any one of a number of commonly known liquid tackifying agents including liquid hydrocarbon resins and hydrogenated hydrocarbon resins, liquid polystyrenes, liquid rosin esters, liquid polyterpenes, liquid resins from polymerized and hydrogenated C9 hydrocarbon streams; liquid resins from polymerized and hydrogenated dicyclopentadiene species; liquid resins from polymerized and hydrogenated pure monomer species such as styrene, vinyl toluene, alphamethyl styrene; oils such as naphthenic oils and paraffinic oils; etc. The liquid tackifying resins include a liquid hydrocarbon resin comprising polymerized structures derived primarily from a stream of aliphatic petroleum derivatives, both dienes and mono-olefins, containing 4 to 6 carbon atoms. This polymerized product may optionally be further hydrogenated. Such resins are commercially available from the Goodyear Chemical Company as WING TACK TM 10 and from the Exxon Chemical Company as ESCOREZ TM 2520. Another useful liquid tackifier resin comprises predominantly cyclopentadiene species that have been polymerized and hydrogenated. Such a tackifying resin is available from Exxon Chemical Company as ECR-327. Another liquid tackifying resin is a resin produced from the polymerization and hydrogenation of a pure monomer feedstock comprising styrene, vinyl toluene, and alphamethyl styrene, such as the resin available from Hercules Chemical Company as REGALREZ TM 1018. Another useful liquid tackifying resin is a polymerized alpha pinene resin having a softening point around 25° C. available from Arizona Chemical Company as ZONAREZ TM A-25. ZONAREZ TM A-25 is especially preferred for formulations containing styrene/butadiene block copolymers.

This invention also contemplates that conventional additives and fillers may be used in the adhesive formulations described for the release and fastening tapes for various purposes. These additives include, but are not limited to, antioxidants such as 2,5di(tertiary amyl) hydroquinone and t-butylcresol, heat stabilizers such as zinc alkyl dithiocarbamates, ultraviolet stabilizers, pigments and coloring agents such as zinc oxide and titanium dioxide, carbon black, clay, calcium carbonate, etc.

A number of methods may be used to produce the adhesive tapes and the closure system described in this invention. The adhesive may be coated using solution coating for the natural rubber-based pressure-sensitive adhesives for the release tape and solution coating, hot-melt gravure coating, hot-melt extrusion coating, etc. for the fastening tape. Solution coating is the preferred method because the high softening point of the preferred reinforcing resins (ENDEX TM 155 and ENDEX TM 160) makes hot-melt coating somewhat more difficult for the fastening tape.

The following examples are given by way of illustration and are not intended to limit the scope of the invention in any way.

EXAMPLES 1-12 AND COMPARATIVE EXAMPLES C1 AND C2

The compositions of Examples 1-12 and Comparative Examples C1 and C2 are given in Table A. IRGANOX TM 1076 is an antioxidant material available from Ciba-Geigy. The remaining raw materials have been described previously. All of the tape samples were prepared by dissolving the ingredients in a 4:1 blend of toluene and heptane at 50% solids by weight. The adhesive solutions were then coated using a knife coater onto a 100 micron polypropylene film and dried in a convection oven for 10 minutes at 60° C. to remove the solvent. The weight of the dried adhesive on the film was 3.5 mg/square centimeter. The tapes produced in this manner were then laminated to a silicone treated release liner and stored at room temperature until testing.

Figure 2:
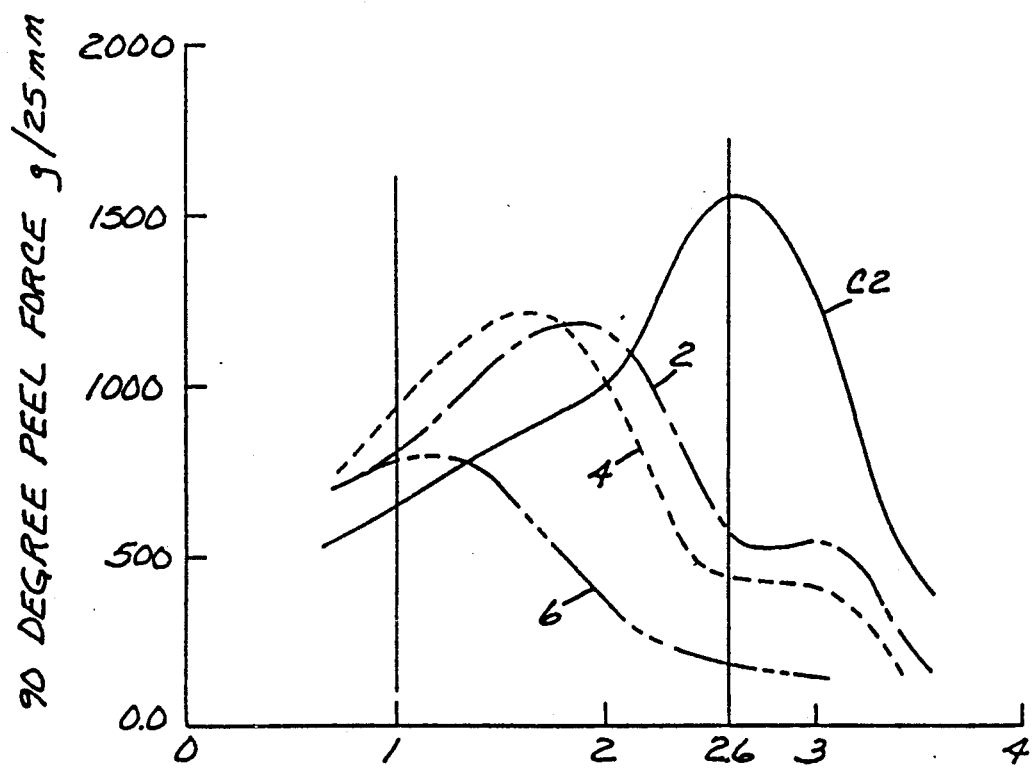
FIG. 2 is a plot of the 90 degree peel force in g/25 cm in relation to the log peel rate in cm/min for the adhesive compositions of Examples 2, 4, and 6 and Comparative Example C2.
Figure 3:
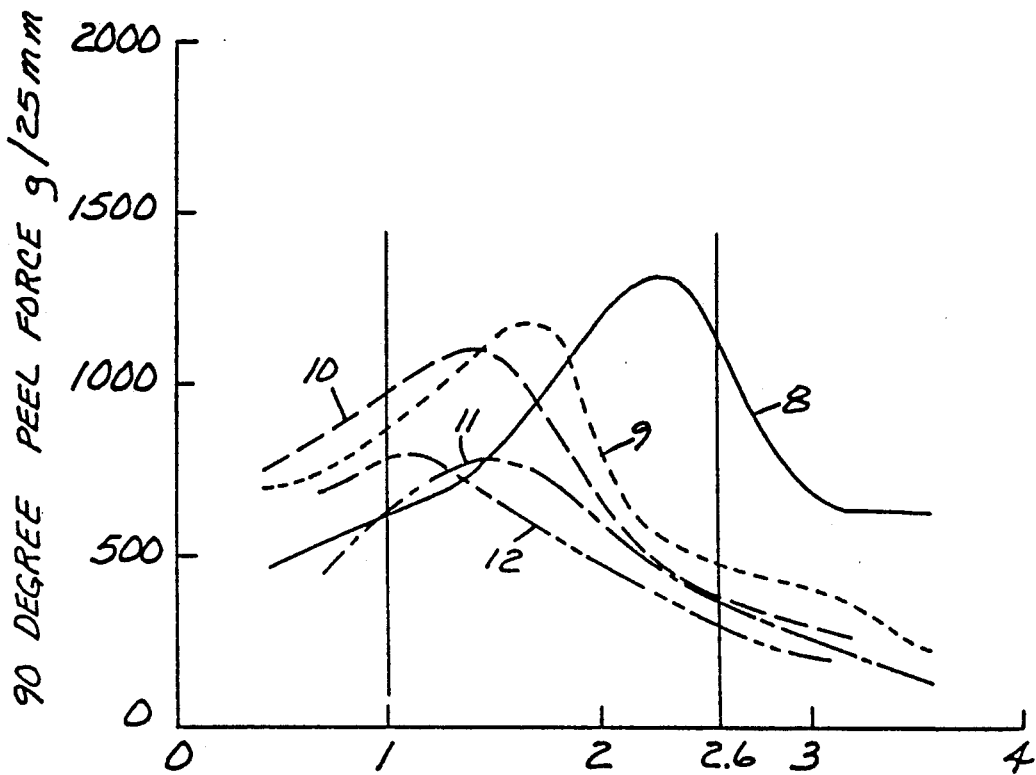
FIG. 3 is a plot of the 90 degree peel force in g/25 cm in relation to the log peel rate in cm/min for the adhesive compositions of Examples 8 to 12.

The tapes were tested to find the maximum in the peel force vs. rate curve as follows. The tape samples were placed onto the polyethylene substrate such as is found in TENDRESSE TM brand disposable diapers manufactured by Colgate-Palmolive in France and were rolled down with a 2 kg. roll down force. The polyethylene in turn was held down to a flat steel panel with a very aggressive double-sided adhesive tape. The test tape was then peeled at an angle of 90 degrees to the substrate at various peel rates in order to determine the peel rate corresponding to the maximum peel force. The peel results are summarized in Table B. Examples incorporating the end block resin displayed a maximum in the peel force between 10 and 400 cm/min, i.e., log peel rate beetween about 1.0 and 2.6 cm/min as shown in FIGS. 1, 2, and 3. In FIG. 1, the solid line represents Comparative Example C1, the dashed line represents Example 1, the dotted line represents Example 3, the dash-dotted line represents Example 5, and the dash-dot-dotted line represents Example 7. In FIG. 2, the solid line represents Comparative Example C2, the dash-dotted line represents Example 2, the dotted line represents Example 4, and the dash-dot-dotted line represents Example 6. In FIG. 3, the solid line represents Example 8, the dotted line represents Example 9, the dashed line represents Example 10, the dash-dotted line represents Example 11, and the dash-dot-dotted line represents Example 12.

Figure 4:
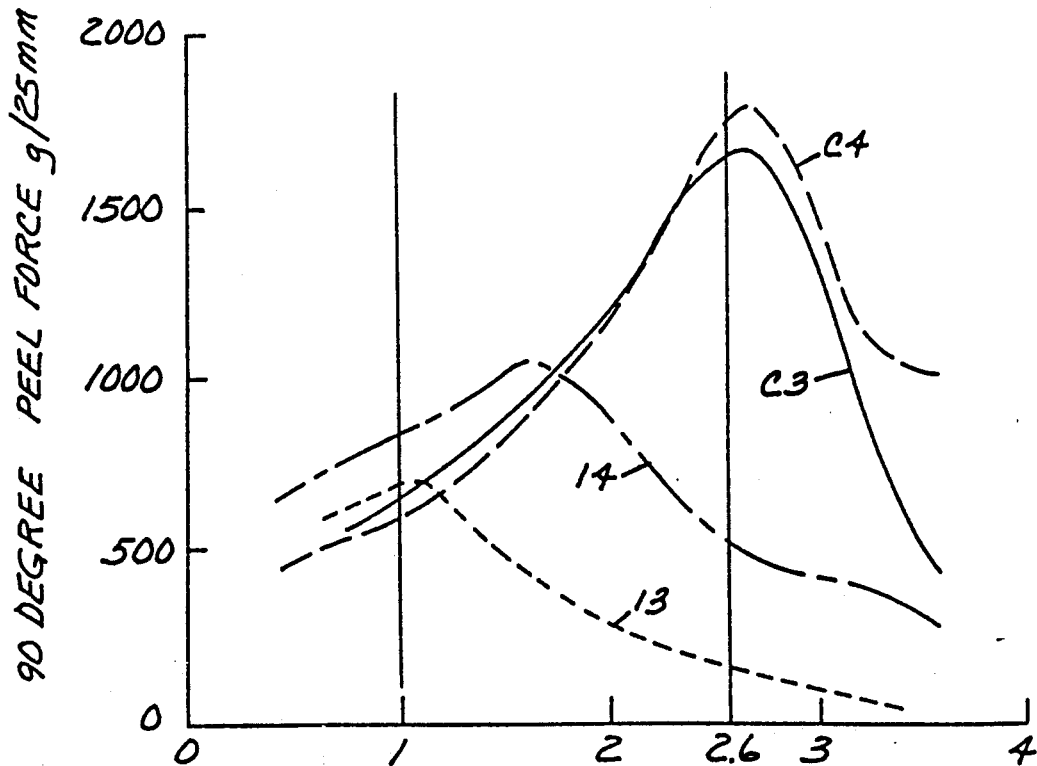
FIG. 4 is a plot of the 90 degree peel force in g/25 cm in relation to the log peel rate in cm/min for the adhesive compositions of Examples 13 and 14 and Comparative Examples C3 and C4.
Figure 5:
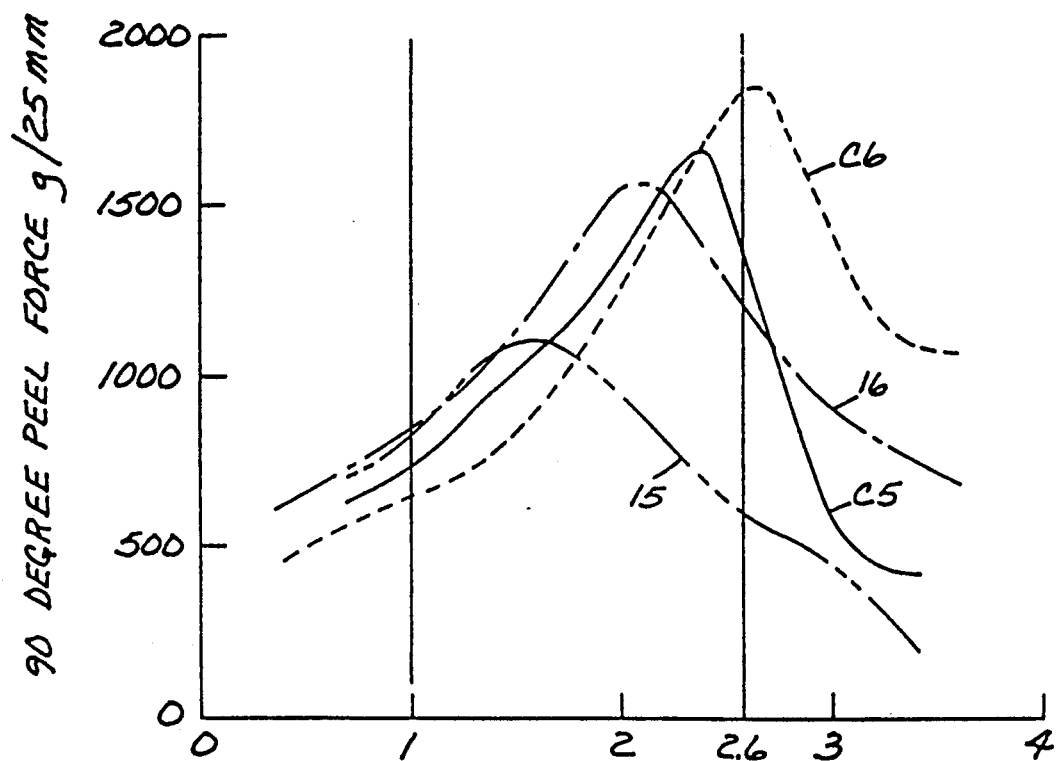
FIG. 5 is a plot of the 90 degree peel force in g/25 cm in relation to the log peel rate in cm/min for the adhesive compositions of Examples 15 and 16 and Comparative Examples C5 and C6.
Figure 6:
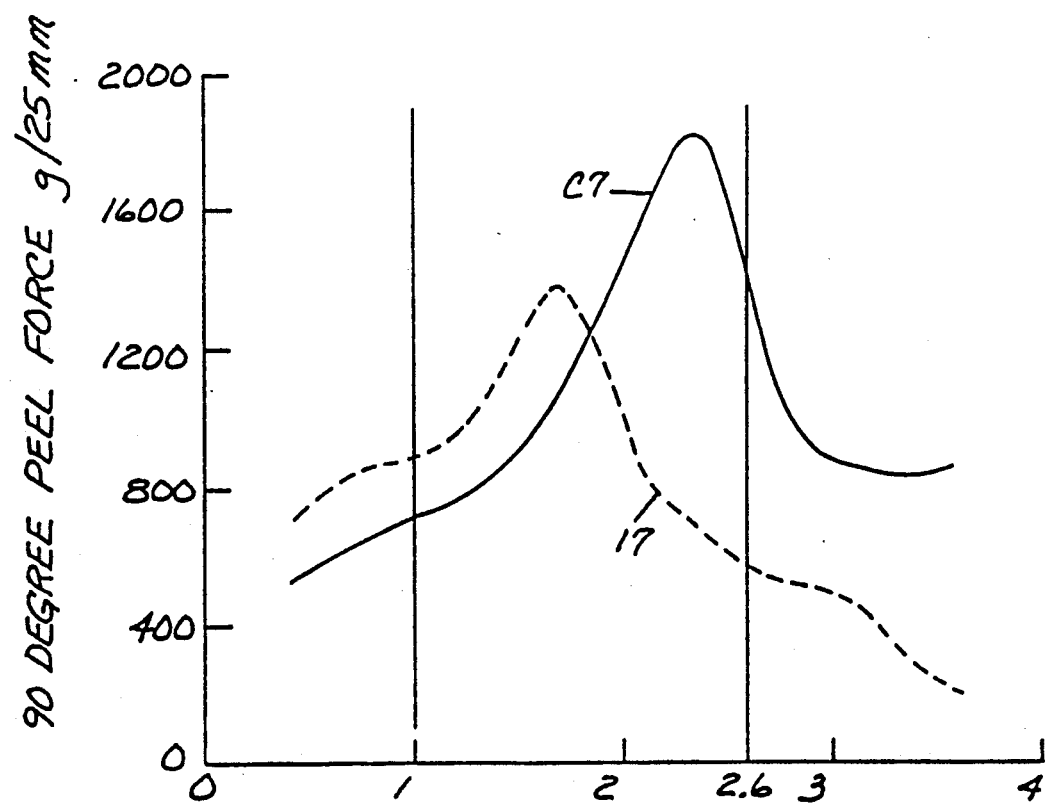
FIG. 6 is a plot of the 90 degree peel force in g/25 cm in relation to the log peel rate in cm/min for the adhesive compositions of Example 17 and Comparative Example C7.

Comparative Examples C3-C7 are given in Table C. The tape samples were prepared and tested in the same manner as in Examples 1-12. The peel results are summarized in Table D. Again examples of the invention incorporating the end block resin display a maximum in the peel force between 10 and 400 cm/min, i.e., log peel rate between about 1.0 and 2.6 as shown in FIGS. 4, 5, and 6. In FIG. 4, the solid line represents Comparative Example C3, the dashed line represents Comparative Example C4, the dotted line represents Example 13, and the dash-dotted line represents Example 14. In FIG. 5, the solid line represents Comparative Example C5, the dotted line represents Comparative Example C6, the dash-dot-dotted line represents Example 15, and the dash-dotted line represents Example 16. In FIG. 6, the solid line represents Comparative Example C7 and the dotted line represents Example 17.

TABLE A

Composition of Examples 1-12 and Comparative Examples C1 and C2
Parts by Weight

| | Example | | | | | | | | | | | | | |
|---|---|---|---|---|---|---|---|---|---|---|---|---|---|---|
| | C1 | C2 | 1 | 2 | 3 | 4 | 5 | 6 | 7 | 8 | 9 | 10 | 11 | 12 |
| KRATON™ 1107 | 35 | 35 | 35 | 35 | 35 | 35 | 35 | 35 | 35 | 35 | 35 | 35 | 35 | 35 |
| ESCOREZ™ 2520 | 34 | 29 | 34 | 29 | 34 | 29 | 34 | 29 | 34 | 39 | 29 | 24 | 39 | 33 |
| ESCOREZ™ 5300 | 31 | 36 | 31 | 36 | 31 | 36 | 31 | 36 | 31 | 26 | 36 | 41 | 26 | 32 |
| ENDEX™ 160 | 0 | 0 | 4 | 5 | 8 | 10 | 12 | 15 | 16 | 8 | 8 | 8 | 15 | 15 |
| IRNGANOX™ 1076 | 1 | 1 | 1 | 1 | 1 | 1 | 1 | 1 | 1 | 1 | 1 | 1 | 1 | 1 |

TABLE B

90 Degree Peel Force at Various Peel Rates
grams per 25 mm

| | Peel Rate, cm/min | | | | | | | | | | |
|---|---|---|---|---|---|---|---|---|---|---|---|
| Example | 2.5 | 5 | 12.5 | 25 | 50 | 125 | 250 | 500 | 1250 | 2500 | 3750 |
| C1 | 410 | 440 | 560 | 650 | 840 | 1200 | 1460 | 1730 | 1180 | 950 | 1000 |
| C2 | — | 550 | 690 | 810 | 915 | 1060 | 1490 | 1550 | 1150 | 450 | 460 |
| 1 | 500 | 550 | 700 | 800 | 1020 | 1360 | 1630 | 1290 | 940 | 880 | 710 |
| 2 | — | 715 | 850 | 1040 | 1160 | 1140 | 770 | 460 | 600 | 225 | 180 |
| 3 | 670 | 700 | 840 | 970 | 1150 | 1000 | 870 | 680 | 540 | 450 | 350 |
| 4 | — | 745 | 980 | 1180 | 1220 | 930 | 490 | 450 | 440 | 170 | — |
| 5 | 710 | 720 | 900 | 1010 | 1180 | 625 | 450 | 400 | 325 | 240 | 210 |
| 6 | — | 705 | 805 | 760 | 590 | 240 | 250 | 180 | 160 | — | — |
| 7 | 650 | 760 | 870 | 760 | 400 | 330 | 350 | 260 | 205 | 130 | 120 |
| 8 | 450 | 550 | 645 | 740 | 930 | 1250 | 1380 | 860 | 630 | 660 | 620 |
| 9 | 700 | 730 | 940 | 1030 | 1210 | 585 | 540 | 430 | 400 | 255 | 220 |
| 10 | 760 | 800 | 990 | 1130 | 960 | 530 | 430 | 330 | 255 | 140 | 140 |
| 11 | — | 440 | 700 | 780 | 740 | 530 | 420 | 370 | 290 | 130 | — |
| 12 | — | 700 | 820 | 710 | 590 | 400 | 370 | 250 | 210 | — | — |

EXAMPLES 13-17 AND COMPARATIVE EXAMPLES C3-C7

Examples 13-17 illustrate the use of different solid tackifier resins in combination with different liquid resins in the embodiment of this invention. In Examples 13-17, the end block resin used is ENDEX TM 160 and in Comparative Examples C3-C7, the end block resin is omitted. The compositions for Examples 13-17 and

TABLE C

Composition of Examples 13-17 and
Comparative Examples C3-C7
Parts by Weight

| | Example | | | | | | | | | |
|---|---|---|---|---|---|---|---|---|---|---|
| | C3 | C4 | 13 | 14 | C5 | C6 | 15 | 16 | C7 | 17 |
| KRATON™ 1107 | 35 | 35 | 35 | 35 | 35 | 35 | 35 | 35 | 35 | 35 |
| WINGTACK™ 10 | 24 | 28 | 24 | 28 | | | | | | |
| ZONAREZ™ A-25 | | | | | 23 | 28 | 23 | 28 | | |
| REGALREZ™ 1018 | | | | | | | | | 30 | 30 |
| PERMALYN™ 1105 | 41 | 37 | 41 | 37 | | | | | | |
| EXCOREZ™ 1310 | | | | | 42 | 37 | 42 | 37 | | |
| REGALREZ™ 1094 | | | | | | | | | 35 | 35 |
| ENDEX™ 160 | 0 | 0 | 15 | 8 | 0 | 0 | 15 | 8 | 0 | 8 |
| IRGANOX™ 1076 | 1 | 1 | 1 | 1 | 1 | 1 | 1 | 1 | 1 | 1 |

TABLE D

90 Degree Peel Force at Various Peel Rates
grams per 25 mm

| Example | Peel Rate, cm/min | | | | | | | | | | |
|---|---|---|---|---|---|---|---|---|---|---|---|
| | 2.5 | 5 | 12.5 | 25 | 50 | 125 | 250 | 500 | 1250 | 2500 | 3750 |
| C3 | — | 560 | 670 | 870 | 1000 | 1260 | 1540 | 1710 | 1100 | 540 | 480 |
| C4 | 435 | 520 | 620 | 760 | 970 | 1230 | 1570 | 1830 | 1200 | 1000 | 1050 |
| 13 | — | 630 | 710 | 540 | 335 | 225 | 210 | 140 | 70 | 40 | — |
| 14 | 630 | 770 | 830 | 930 | 1100 | 760 | 585 | 445 | 425 | 360 | 260 |
| C5 | — | 640 | 770 | 990 | 1120 | 1400 | 1700 | 1130 | 460 | 455 | — |
| C6 | 450 | 570 | 670 | 780 | 985 | 1340 | 1650 | 1880 | 1220 | 1090 | 1100 |
| 15 | — | 710 | 890 | 1100 | 1110 | 920 | 625 | 560 | 470 | 180 | — |
| 16 | 630 | 730 | 890 | 1080 | 1260 | 1610 | 1390 | 1070 | 855 | 760 | 710 |
| C7 | 530 | 640 | 740 | 850 | 1100 | 1560 | 1850 | 1140 | 880 | 830 | 870 |
| 17 | 700 | 850 | 920 | 1100 | 1400 | 840 | 680 | 530 | 480 | 270 | 220 |

EXAMPLES 18-21

Figure 7:
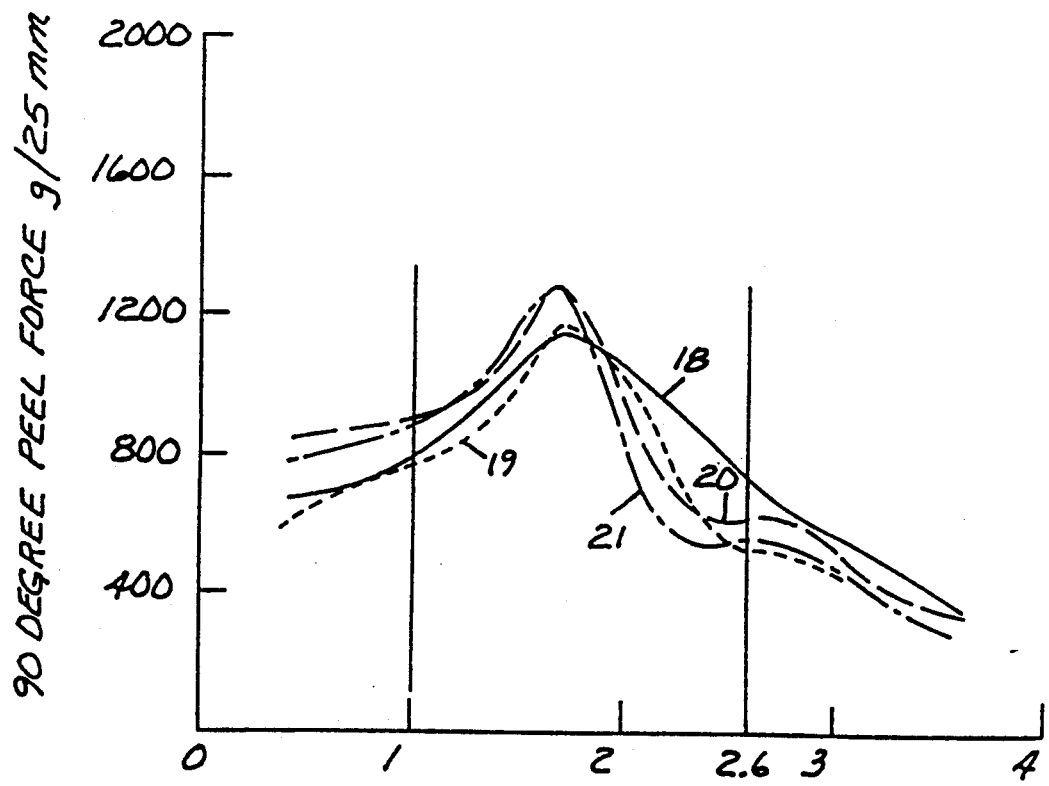
FIG. 7 is a plot of the 90 degree peel force in g/25 cm in relation to the log peel rate in cm/min for the adhesive compositions of Examples 18 to 21.

Examples 18-21 illustrate the similarity in peel properties when a typical embodiment of this invention (Example 5) is peeled from a variety of different diaper polyethylene substrates. The substrates used are as follows. Example 18 utilizes a polyethylene film such as is found on TENDRESS TM brand disposable diapers manufactured by Colgate-Palmolive in France. Example 19 employs a polyethylene film such as is found on HUGGIES TM brand disposable diapers manufactured by Kimberly-Clark. This film is more completely described in U.S. Pat. No. 4,655,761. Example 20 uses a polyethylene film such as is found on LUV's TM brand disposable diapers manufactured by the Proctor and Gamble Company. Finally, Example 21 demonstrates the peel properties from a polyethylene film such as is found on BABY's FAVORITE TM brand disposable diapers manufactured by Weyerhaueser. The examples were subjected to the same peel test as in Examples 1-12. The peel results are summarized in Table E and plotted as log peel rates in FIG. 7, the log peel rates of 1.0 and 2.6 cm/min being equivalent to peel rates of 10 and 400 cm/min, respectively. In FIG. 7, the solid line represents Example 18, the dotted line represents Example 19, the dashed line represents Example 20, and the dash-dotted line represents Example 21.

TABLE E

90 Degree Peel Force at Various Peel Rates
grams per 25 mm

| Example | Peel Rate, cm/min | | | | | | | | | | |
|---|---|---|---|---|---|---|---|---|---|---|---|
| | 2.5 | 5 | 12.5 | 25 | 50 | 125 | 250 | 500 | 1250 | 2500 | 3750 |
| 18 | 670 | 700 | 840 | 970 | 1150 | 1000 | 870 | 680 | 540 | 450 | 350 |
| 19 | 600 | 700 | 810 | 910 | 1150 | 930 | 560 | 540 | 430 | 330 | 280 |
| 20 | 840 | 870 | 920 | 1060 | 1310 | 820 | 620 | 640 | 470 | 370 | 350 |
| 21 | 770 | 820 | 920 | 1050 | 1290 | 660 | 550 | 560 | 440 | 320 | 280 |

EXAMPLES 22-25 AND COMPARATIVE EXAMPLE C8

Table F gives the adhesive formulations in parts by weight prepared for Examples 22-25 and Comparative Example C8. The tape samples were prepared in the same manner as Examples 1-12. Table G gives the peel force and rate data for Comparative Example C8 and Examples 22-25. These tape samples were tested in the following manner. Strips 25 mm wide and 100 mm long were cut from the tape samples. The strips were placed on a 35 micron corona treated polyethylene substrate such as is found on HUGGIES TM brand disposable diapers (manufactured by Kimberly-Clark) and were rolled down using a 2 kg roller and 2 passes. The tape strips were subsequently peeled at 180 degrees at various peel rates using an MTS Model 810 Materials Testing System. The test procedure is that called for in the 180 degree peel adhesion test described in Pressure Sensitive Adhesive Tape Council, PSTC-1.

Figure 8:
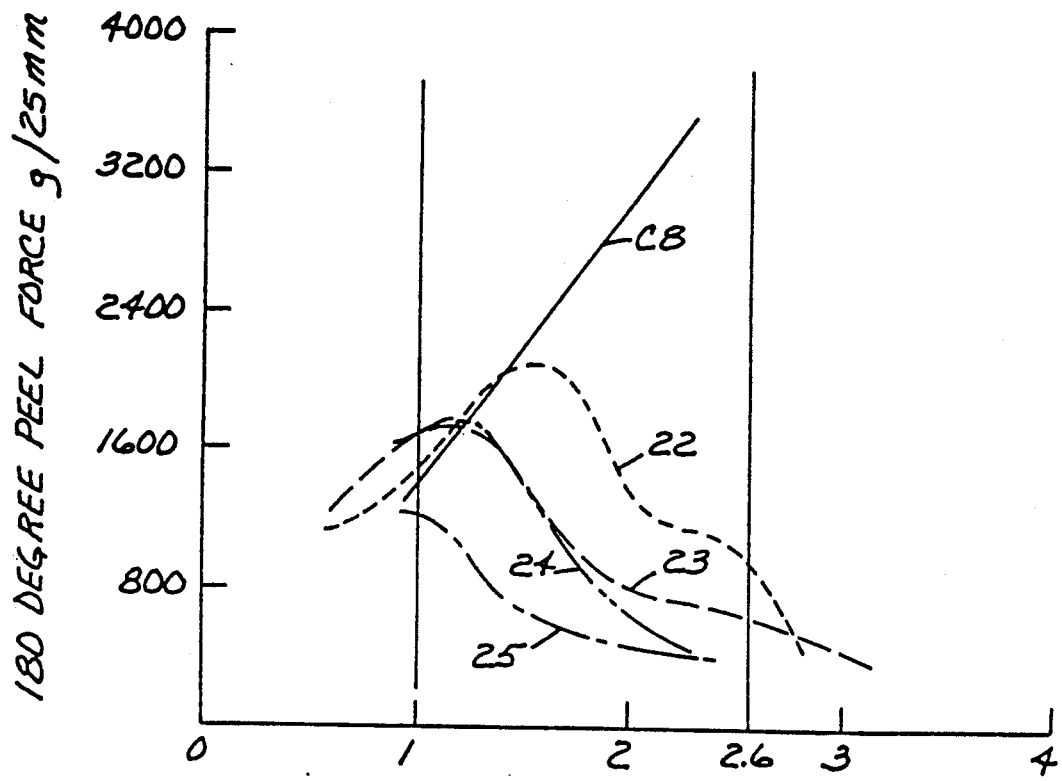
FIG. 8 is a plot of the 180 degree peel force in g/25 cm in relation to the log peel rate in cm/min for the adhesive compositions of Examples 22 to 25 and Comparative Example C8.

When no end block resin is used, as in Example C8 as taught by U.S. Pat. No. 3,932,328, no maximum in the peel force vs. rate curve is seen below 400 cm/min. In fact, the peel force increases monotonically with rate until the peel force exceeds the strength of the tape backing. In this case the backing breaks before the tape peels from the substrate. Upon the addition of 5, 10, 15, and 20% Endex 160 end block resin as described in this invention, it was discovered that a maximum in the peel force vs. peel rate between 10 and 400 cm/min occurred. This can further be seen in FIG. 8 where log peel values are between about 1.0 and 2.6 cm/min which correspond to peel values of 10 and 400 cm/min, respectively. In FIG. 8, the solid line represents Comparative Example C8, the dotted line represents Example 22, the dashed line represents Example 23, the dash-dot-dotted line represents Example 24, and the dash-dotted line represents Example 25.

TABLE F

Composition of Examples 29-33
Parts by Weight

| | Example | | | | |
|---|---|---|---|---|---|
| | C8 | 22 | 23 | 24 | 25 |
| KRATON TM 1107 | 37 | 37 | 37 | 37 | 37 |
| ZONAREZ TM A-25 | 14 | 14 | 14 | 14 | 14 |
| ESCOREZ TM 1310 | 49 | 49 | 49 | 49 | 49 |
| ENDEX TM 160 | 0 | 5 | 10 | 15 | 20 |
| IRGANOX TM 1076 | 1 | 1 | 1 | 1 | 1 |

TABLE G

| | 180 Degree Peel Force at Various Peel Rates grams per 25 mm | | | | | | | | | |
|---|---|---|---|---|---|---|---|---|---|---|
| | Peel Rate, cm/min | | | | | | | | | |
| Example | 4 | 8 | 15 | 25 | 50 | 100 | 200 | 320 | 640 | 1280 |
| C8 * | — | 1240 | 1650 | 2040 | 2460 | 2970 | >3500 | >3500 | >3500 | — |
| 22 | 1140 | 1350 | 1650 | 2070 | 2040 | 1260 | 1150 | 1060 | 480 | — |
| 23 | 1250 | 1550 | 1830 | 1600 | 1050 | 780 | 730 | 670 | 510 | 390 |
| 24 | — | 1550 | 1790 | 1680 | 930 | 600 | 480 | — | — | — |
| 25 | — | 1210 | 1150 | 660 | 470 | 470 | 420 | 400 | — | — |

* At peel rates above 200 cm/min the peel force exceeded the tensile strength of the polypropylene film backing

EXAMPLES 26-34

The tape samples were prepared in the same manner as Examples 1-12 using the formulations in Table H. In addition to determining the peel rate corresponding to the maximum peel force using the test described for Examples 1-12, the tape samples were also tested for reopenability. The samples were applied as tape tabs to commercially available disposable diapers that had a 1.4 mil polyethylene backsheet. The diapers used were the TENDRESSE TM brand disposable diaper manufactured by Colgate-Palmolive in France. The closure system now incorporating the example tapes was closed and subsequently reopened after having remained closed for 4 hours. A successful reopening leaves the polyethylene undamaged. Table I shows the rate at which the peel force reaches a maximum for these examples as well as the percent of the tabs tested for reopenability that passed the reopening test.

TABLE H

| Composition of Examples 26-34 Parts by Weight | | | | | | | | | |
|---|---|---|---|---|---|---|---|---|---|
| | Example | | | | | | | | |
| | 26 | 27 | 28 | 29 | 30 | 31 | 32 | 33 | 34 |
| KRATON TM 1107 | 37 | 37 | 37 | 37 | 37 | 37 | 37 | 37 | 37 |
| ZONAREZ TM A-25 | 22 | 18 | 14 | 22 | 18 | 14 | 22 | 18 | 14 |
| ESCOREZ TM 1310 | 41 | 45 | 49 | 41 | 45 | 49 | 41 | 45 | 49 |
| ENDEX TM 160 | 2 | 2 | 2 | 5.5 | 5.5 | 5.5 | 9 | 9 | 9 |
| IRGANOX TM 1076 | 1 | 1 | 1 | 1 | 1 | 1 | 1 | 1 | 1 |

TABLE I

| Example | Rate for Maximum Peel Force cm/min | Percent Reopenability |
|---|---|---|
| 26 | 225 | 85 |
| 27 | 180 | 100 |
| 28 | 180 | 95 |
| 29 | 180 | 95 |
| 30 | 180 | 40 |
| 31 | 140 | 95 |
| 32 | 180 | 95 |
| 33 | 140 | 100 |
| 34 | 120 | 100 |

EXAMPLE 35 AND COMPARATIVE EXAMPLE C9

Figure 9:
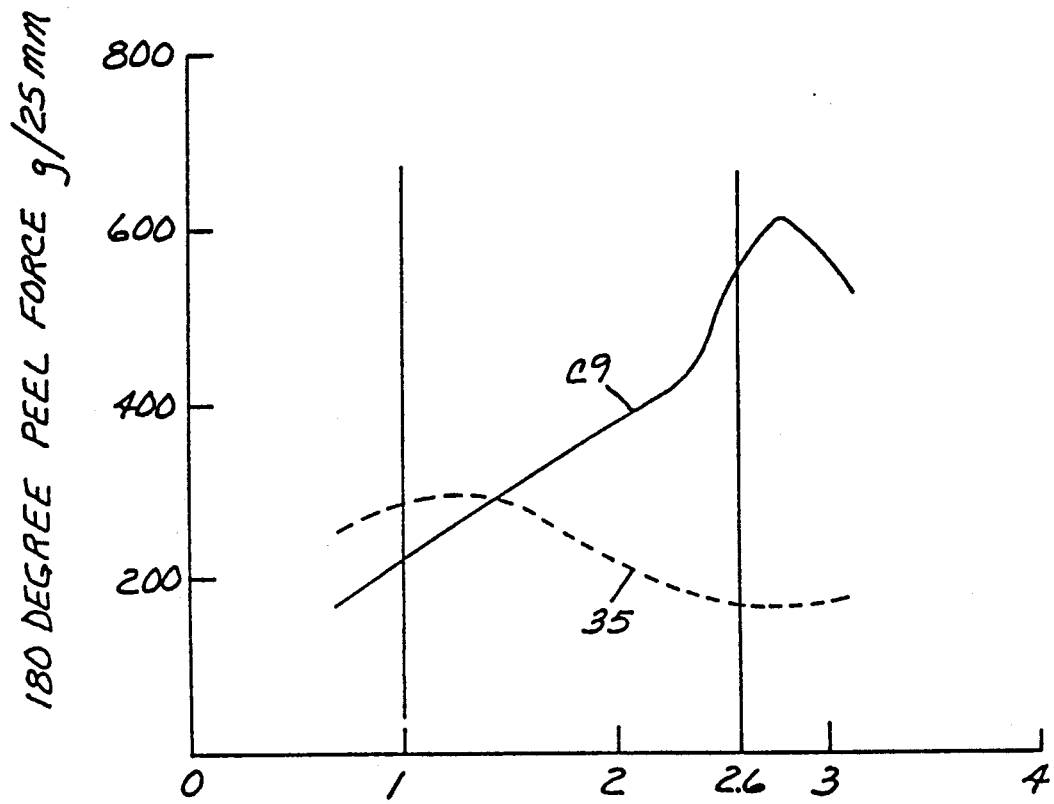
FIG. 9 is a plot of the 180 degree peel force in g/25 cm in relation to the log peel rate in cm/min for the adhesive compositions of Example 35 and Comparative Example C9.

The following two examples were coated from a 4:1 toluene/heptane solution (50% solids) as previously described onto a polypropylene backing. Example C9 is the same as Example 3 from U.S. Pat. No. 3,932,328. It contains 100 parts KRATON TM 1107, 100 parts WING TACK TM 10, and 100 parts WING TACK TM 95. Example 35 contains the same amount of all of these raw materials but it also includes 50 parts of an end block reinforcing resin ENDEX TM 160. The peel test used on these two examples is the same as for Examples 22-25. The results are summarized in Table J. The example from U.S. Pat. No. 3,932,328 does not exhibit the unique maximum in peel force vs. rate curve between 10 cm/min and 400 cm/min. This is further demonstrated in FIG. 9, where the solid line represents Comparative Example C9 and the dotted line represents Example 35.

TABLE J

| | 180 Degree Peel Force at Various Peel Rates grams per inch | | | | | | | |
|---|---|---|---|---|---|---|---|---|
| | Peel Rate cm/min | | | | | | | |
| Example | 5 | 12.5 | 25 | 50 | 125 | 250 | 500 | 1250 |
| C9 | 170 | 240 | 290 | 330 | 400 | 430 | 620 | 530 |
| 35 | 250 | 290 | 330 | 250 | 210 | 170 | 170 | 180 |

EXAMPLE 36 AND COMPARATIVE EXAMPLE C10

Figure 10:
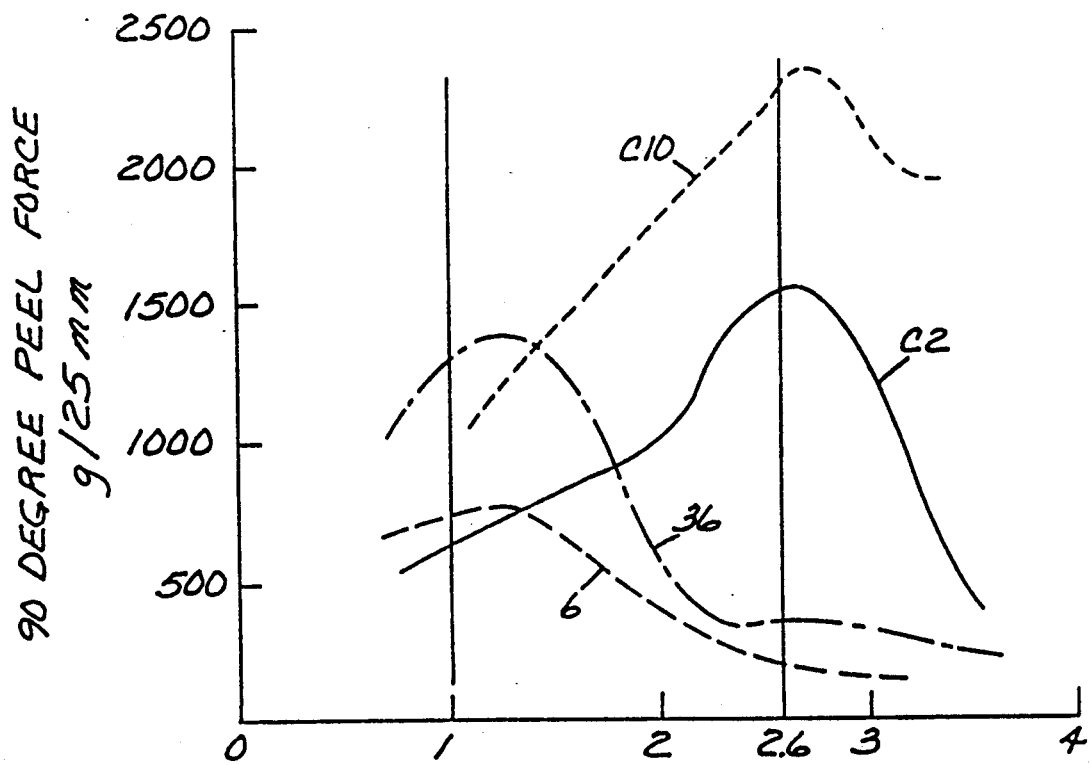
FIG. 10 is a plot of the 90 degree peel force in g/25 cm in relation to the log peel rate in cm/min for the adhesive compositions of Examples 8 and 36 and Comparative Examples C2 and C10.

Comparative Example C10 and Example 36 use the same adhesive tapes as were used for Comparative Example C2 and Example 6, respectively. The peel test was the same 90 degree peel test as was used in Examples 1-12. The substrate for these examples was polypropylene instead of polyethylene. As can be seen from the data in Table K and the plot in FIG. 10, the polypropylene substrate does not change the general performance of the adhesives of this invention -- the maximum in the peel force is seen at peel rates between 10 and 400 cm/min, i.e., log peel rates between about 1.0 and 2.6 cm/min. In FIG. 10, the solid line represents Comparative Example C2, the dotted line represents Comparative Example C10, the dashed line represents Example 6, and the dash-dotted line represents Example 36.

TABLE K

| | 90 Degree Peel Force at Various Peel Rates grams per inch | | | | | | | | | | |
|---|---|---|---|---|---|---|---|---|---|---|---|
| | Peel Rate, cm/min | | | | | | | | | | |
| Ex. | 2.5 | 5 | 12.5 | 25 | 50 | 125 | 250 | 500 | 1250 | 2500 | 3750 |
| C2 | — | 550 | 690 | 810 | 915 | 1060 | 1490 | 1550 | 1150 | 450 | 460 |
| C10 | — | — | 1050 | 1360 | 1510 | 1910 | 2060 | 2390 | 2020 | 1950 | — |
| 6 | — | 705 | 805 | 760 | 590 | 240 | 250 | 180 | 160 | — | — |

TABLE K-continued

| | 90 Degree Peel Force at Various Peel Rates grams per inch | | | | | | | | | | |
|---|---|---|---|---|---|---|---|---|---|---|---|
| | Peel Rate, cm/min | | | | | | | | | | |
| Ex. | 2.5 | 5 | 12.5 | 25 | 50 | 125 | 250 | 500 | 1250 | 2500 | 3750 |
| 36 | 1000 | 980 | 1370 | 1360 | 1060 | 330 | 350 | 400 | 270 | 280 | 240 |

Various modifications and alterations of this invention will become apparent to those skilled in the art without departing from the scope and spirit of this invention.

What is claimed is:

1. A pressure-sensitive adhesive composition comprising an elastomer which is an A-B-A block copolymer, wherein the A blocks are derived from styrene or alphamethylstyrene and the B blocks are derived from isoprene, butadiene, or hydrogenated versions thereof or an (AB) block copolymer of the same type of composition in another geometry such as a tapered block copolymer or a radial block copolymer, a solid tackifier resin, a liquid tackifier resin, and an end block reinforcing resin.

2. A pressure-sensitive adhesive composition according to claim 1 wherein the elastomeric component is present in the range of from 20 to 50 percent by weight, the solid tackifying resin is present in the range of from 20 to 60 percent by weight, the liquid tackifying resin is present in the range of from 10 to 40 percent by weight and the end block reinforcing resin is present in the range from 2 to 20 percent by weight.

3. A pressure-sensitive adhesive composition according to claim 1 wherein the elastomeric component is present in the range of from 25 to 40 percent by weight, the solid tackifying resin is present in the range of from 25 to 50 percent by weight, the liquid tackifying resin is present in the range of from 15 to 30 percent by weight and the end block reinforcing resin is present in the range of from 4 to 14 percent by weight.

4. A pressure-sensitive adhesive composition according to claim 3 wherein the A blocks of the elastomeric component comprises from 8 to 30 percent by weight of the total block copolymer when the B block is isoprene-based and from 20 to 50 percent by weight of the total block copolymer when the B block is butadiene based, the molecular weight of the total block copolymer being above 50,000.

5. A pressure-sensitive adhesive composition according to claim 3 wherein the solid tackifying resin comprises rosin esters, hydrogenated rosin esters, polyterpene resins, polymerized hydrocarbon resins based on piperylene, isoprene and conjugated dienes containing 4 to 6 carbon atoms and hydrogenated versions thereof, resins from polymerized and hydrogenated C9 hydrocarbon streams, resins from polymerized and hydrogenated dicyclopentadiene species, resins from polymerized and hydrogenated pure monomer systems such as styrene, vinyl toluene, and alphamethylstyrene.

6. A pressure-sensitive adhesive composition according to claim 3 wherein the liquid tackifying resin comprises liquid hydrocarbon resins and hydrogenated hydrocarbon resins, liquid polystyrene, liquid rosin esters, liquid polyterpenes, liquid resins for polymerized and hydrogenated C9 hydrocarbon streams, liquid resins from polymerized and hydrogenated dicyclopentadiene species, liquid resins from polymerized and hydrogenated pure monomer species such as styrene, vinyl toluene, alphamethylstyrene, oils such as naphthenic oils and paraffinic oils.

7. A pressure-sensitive adhesive composition according to claim 3 wherein the end block reinforcing resin comprises low molecular weight polymers of styrene and alphamethylstyrene and copolymers thereof, said end block reinforcing resin having a glass transition temperature higher than the service temperature of the pressure-sensitive adhesive.

* * * * *

UNITED STATES PATENT AND TRADEMARK OFFICE
CERTIFICATE OF CORRECTION

PATENT NO. : 5,028,646

DATED : July 2, 1991

INVENTOR(S) : John A. Miller and Egbert A. von Jakusch

It is certified that error appears in the above-identified patent and that said Letters Patent is hereby corrected as shown below:

On title page, item [63] at end of sentence, following the word "abandoned" add the following: -- , which is a continuation-in-part of Ser. No. 07/091,122, Aug. 31, 1987, abandoned --

Col. 1, line 7   "abandoned." should read -- abandoned, and a continuation-in-part of application Ser. No. 07/091,122, filed August 31, 1991, now abandoned.

Col. 8, line 28   "2,5di(tertiary amyl)" should read --2,5-di(tertiary amyl)--

Col. 9, Table A   "IRNGANOX$^{TM}$" should read -- IRGANOX$^{TM}$ --

Col. 11, line 25   "TENDRESS" should read -- TENDRESSE --

Col. 11, line 35   "BABY's FAVORITE" should read -- BABY'S FAVORITE --

Signed and Sealed this

Nineteenth Day of January, 1993

*Attest:*

DOUGLAS B. COMER

*Attesting Officer*   Acting Commissioner of Patents and Trademarks